United States Patent
Weaver et al.

(10) Patent No.: US 11,262,355 B2
(45) Date of Patent: *Mar. 1, 2022

(54) SYSTEM AND APPARATUS FOR POROUSLY-ENCAPSULATED MAGNETIC-NANOPARTICLE BIOSENSORS

(71) Applicant: THE TRUSTEES OF DARTMOUTH COLLEGE, Hanover, NH (US)

(72) Inventors: John B. Weaver, Hanover, NH (US); Barjor Gimi, Jamaica Plain, MA (US); Karl Griswold, Lyme, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/708,302

(22) Filed: Dec. 9, 2019

(65) Prior Publication Data

US 2020/0110085 A1    Apr. 9, 2020

Related U.S. Application Data

(63) Continuation of application No. 14/408,041, filed as application No. PCT/US2013/004589 on Jun. 14, 2013, now Pat. No. 10,502,735.

(60) Provisional application No. 61/659,788, filed on Jun. 14, 2012.

(51) Int. Cl.
  *G01N 33/543* (2006.01)
  *G01N 27/74* (2006.01)
  *G01R 33/12* (2006.01)
  *A61B 5/055* (2006.01)

(52) U.S. Cl.
  CPC ....... *G01N 33/54366* (2013.01); *A61B 5/055* (2013.01); *G01N 27/745* (2013.01); *G01N 33/54326* (2013.01); *G01R 33/1269* (2013.01)

(58) Field of Classification Search
  CPC ........... G01N 33/54366; G01N 27/745; G01N 33/54326; A61B 5/055; G01R 33/1269
  See application file for complete search history.

(56) References Cited

U.S. PATENT DOCUMENTS

| | | |
|---|---|---|
| 6,825,655 B2 | 11/2004 | Minchole et al. |
| 7,639,359 B2 | 12/2009 | Chung et al. |
| 2005/0202075 A1 | 9/2005 | Pardridge et al. |
| 2007/0020310 A1 | 1/2007 | Gracias et al. |
| 2009/0311190 A1 | 12/2009 | Gracias et al. |
| 2011/0059444 A1 | 3/2011 | Stromberg et al. |

OTHER PUBLICATIONS

Rauwerdink, et al., "Measurement of Molecular Binding Using the Brownian Motion of Magnetic Nanoparticle Probes," Applied Physics Letters, vol. 96, Issue 3, pp. 1-3, 2010.
PCT Patent Application PCT/US2013/045896 International Search Report and Written Opinion dated Aug. 21, 2013, 16 pages.

*Primary Examiner* — Robert S Cabral
(74) *Attorney, Agent, or Firm* — Lathrop GPM LLP

(57) ABSTRACT

A system for measuring analyte concentrations has porous-walled nanocontainers containing multiple magnetic nanoparticles, the magnetic nanoparticles coated with a selective binder that is analyte-responsive and binds a the analyte, an indicator substance releasable from the selective binder by the analyte, or an indicator substance cleavable by the analyte, apparatus for exposing the nanocontainers to a fluid potentially containing the analyte, and magnetic spectroscopy of Brownian motion sensing apparatus for detecting agglutination of the nanoparticles or binding of analyte to the nanoparticles. The system is used in a method comprising coating magnetic nanoparticles with a selective binder, encapsulating the magnetic nanoparticles in porous nanocontainers, exposing the nanocontainers to a fluid potentially containing analyte, using magnetic spectroscopy of Brownian motion sensing apparatus to detect agglutination or binding of the nanoparticles, and translating Brownian motion spectra to analyte concentrations.

21 Claims, 5 Drawing Sheets

SYSTEM AND APPARATUS FOR POROUSLY-ENCAPSULATED MAGNETIC-NANOPARTICLE BIOSENSORS

RELATED APPLICATIONS

The present application is a continuation of U.S. patent application Ser. No. 14/408,041 with a § 371(c) date of Dec. 15, 2014, which is a 35 U.S.C. § 371 filing of International Application No. PCT/US13/45896, filed Jun. 14, 2013, which claims priority to U.S. Provisional Patent Application No. 61/659,788, filed Jun. 14, 2012. All of the above-mentioned applications are herein incorporated by reference in their entirety.

GOVERNMENT INTEREST

This invention was made with government support under 1U54CA151662-01 awarded by the National Institutes of Health-National Cancer Institute. The government has certain rights in the invention.

FIELD

The present document describes biosensors fabricated from multiple biosensing nanoparticles encapsulated in porous nanocontainers.

BACKGROUND

Proteins and other molecules such as nucleic acids often have active sites that are capable of binding compounds of interest, or analytes, with great specificity. Highly selective biosensors having a protein, such as an enzyme, antibody, aptamer or other molecule, capable of selectively binding such analytes are known in the art. Some such sensors make use of a chemical reaction catalyzed by the protein as part of providing a detectable signal. In other sensors, such as surface plasmon sensors, binding of the compound of interest to the protein causes a physical change in a resonance that can be detected by suitable equipment.

It is known that small nanoparticles undergo a random motion induced by impact with randomly moving molecules called Brownian motion. Brownian motion can be detected and monitored with a technique called Magnetic Spectroscopy of Nanoparticle Brownian Motion (MSB), described in an article published as A. M. Rauwerdink, J. B. Weaver, "Measurement of Molecular Binding Using The Brownian Motion of Magnetic Nanoparticle Probes" Applied Physics Letters 96, 033702 (2010) and on the web in Feb. 1, 2010 issue of Virtual Journal of Biological Physics Research. The method also appears on the web at http://engineering.dartmouth.edu/reu/documents/CharlieTsai FinalReport.pdf, and for which a copy is attached as an appendix hereto, the contents of which are incorporated herein by reference. It is also known that Brownian motion is a function of particle size, with larger, heavier, particles exhibiting smaller displacements than smaller, lighter, particles.

Magnetic nanoparticles, which typically have cores of either iron or iron oxide, have been coated with proteins or other molecules capable of selectively binding to analytes. When such particles are in suspension, a change in Brownian motion as measured by MSB can be detected when the particles are exposed to the analytes. Strong signal changes occur when multiple nanoparticles bind to the same analyte molecules and therefore agglutinate or aggregate—agglutinated nanoparticles effectively forming fewer but larger and heavier nanoparticles in the suspension; similar signal changes occur when the analyte binds nanoparticles to larger structures such large beads or the solid surfaces. However, changes also occur when individual molecules of analyte bind individual nanoparticles.

SUMMARY

A system for measuring an analyte concentration in a solution has a plurality of nanocontainers suspended in the solution, each nanocontainer having porous walls, at least some nanocontainers containing a plurality of magnetic nanoparticles, the magnetic nanoparticles being coated with a selective binder such as a protein, aptamer, or other molecule capable of selectively binding the analyte, an indicator substance releasable from the selective binder by the analyte, or an indicator substance cleavable by the analyte; and magnetic spectroscopy of Brownian motion sensing apparatus for detecting agglutination of the nanoparticles or another change in the rotational freedom, hemodynamic or magnetic properties of the nanoparticles.

An embodiment is a system for measuring analyte concentrations has porous-walled nanocontainers containing multiple magnetic nanoparticles, the magnetic nanoparticles coated with a substance that selectively binds the analyte, apparatus for exposing the nanocontainers to a fluid potentially containing the analyte, and magnetic spectroscopy of Brownian motion sensing apparatus for detecting agglutination of the nanoparticles.

In another embodiment, a system is used in a method comprising coating magnetic nanoparticles with a selective binding substance, encapsulating the magnetic nanoparticles in porous nanocontainers, exposing the nanocontainers to a fluid, using magnetic spectroscopy of Brownian motion sensing apparatus to detect agglutination or binding of the nanoparticles, and translating Brownian motion spectra to analyte concentrations.

In another embodiment, the nanoparticles would be bound together or to other beads in the probe until the analyte either breaks them free as an enzymatic action on the linking molecules or the analyte could displace the linking molecules through higher affinity bonds.

BRIEF DESCRIPTION OF THE FIGURES

FIG. 5 is an illustration of the apparatus of FIG. 3 with added bias and sweep coils for localizing concentrations of nanoparticles in the

DETAILED DESCRIPTION OF THE EMBODIMENTS

Techniques for forming porous nanocontainers are known, and have been published in PCT/US2006/028564, published as WO2007014113, the contents of which are incorporated herein by reference. Alternatively other small, and potentially metabolizable, nanocontainers that are porous to the analyte but may contain nanoparticles might be used instead of the nanocontainers described in PCT/US2006/028564. The nanocontainers can be any size where the size is selected for its function or method of delivery.

It is proposed that magnetic nanoparticles of a first size be coated with a selective binder, such as selective-binding proteins, aptamer, or other molecules capable of selectively binding an analyte, where the analyte can pass through pores of a second size smaller than the first size. Further, multiples of these nanoparticles are then encapsulated in each of multiple nanocontainers. The pore size of walls of each nanocontainer is selected to be between the first and second sizes, such that the magnetic nanoparticles in each nanocontainer are contained within that nanocontainer. The selective binder is typically determined individually for each analyte with which the system is to be used.

Figure 1:
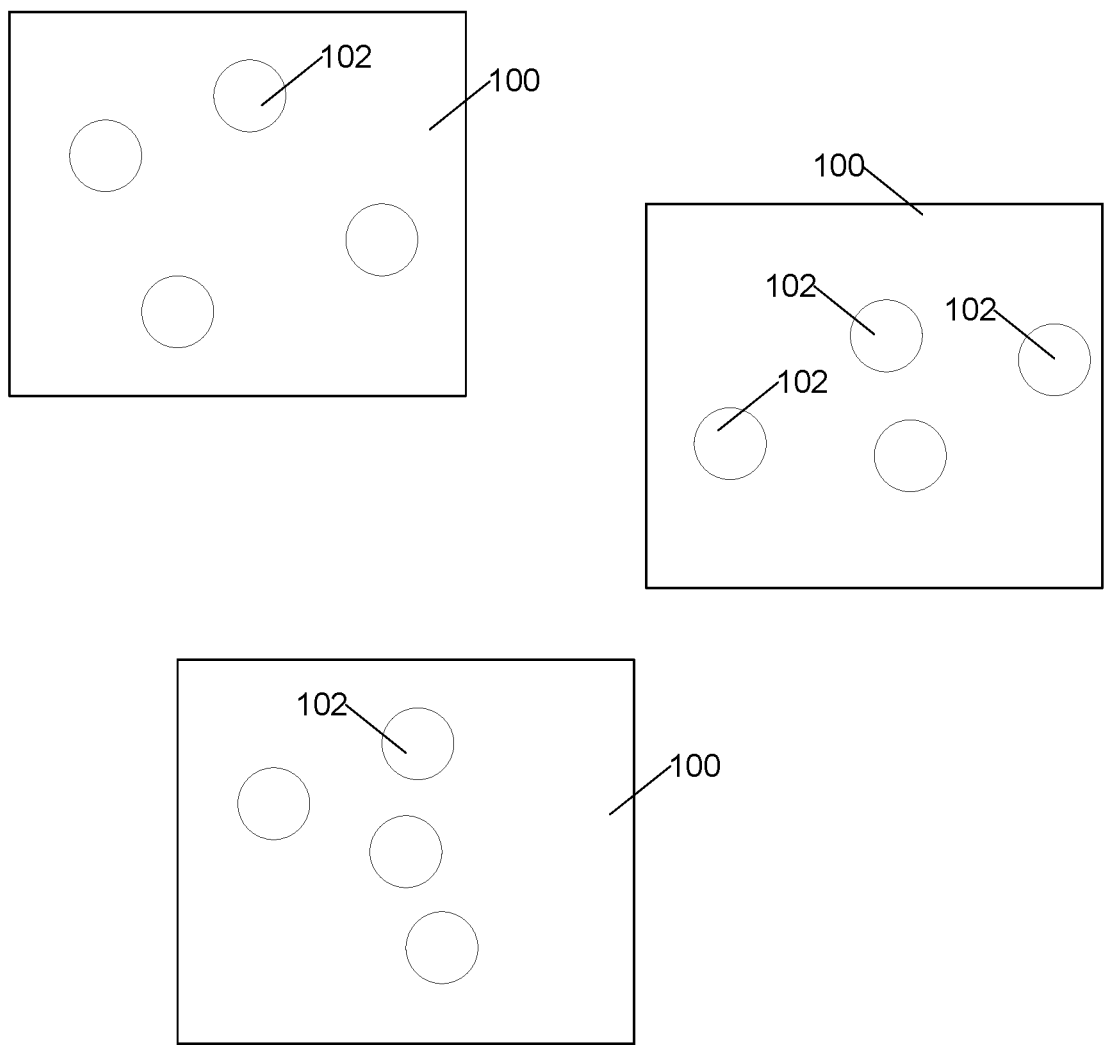
FIG. 1 is a schematic illustration that illustrates multiple protein-coated nanoparticles in a nanocontainer.

Multiple nanocontainers 100 are shown in suspension in FIG. 1 without analyte present. Each nanocontainer has multiple protein-coated, or aptamer-coated, nanoparticles 102 within it. Nanoparticles 102 are separated from each other, moving by Brownian motion within their associated nanocontainers 100.

Figure 2:
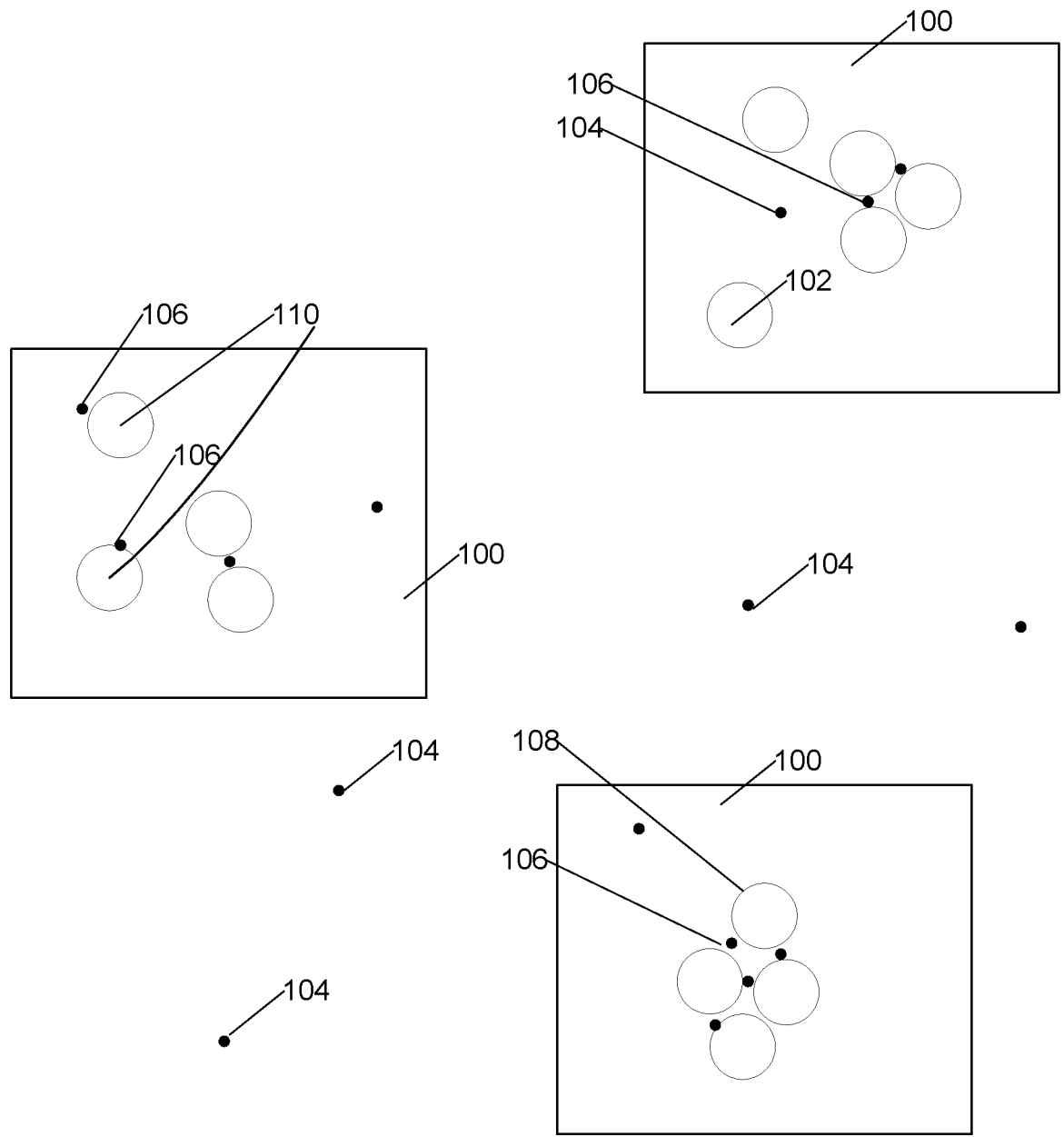
FIG. 2 is a schematic illustration that illustrates multiple protein-coated nanoparticles in a nanocontainer with an analyte present.

In the presence of analyte 104 particles or molecules (FIG. 2), analyte particles 104 may diffuse through pores in nanocontainer walls to enter the nanocontainers. Once within the nanocontainers, analyte particles 104 may bind the selective-binding molecules adherent to each nanoparticle; in some embodiments this binding is reversible and a percentage of nanoparticles bound is dependent on a concentration of the analyte. At least four potential mechanisms to alter the Brownian motion exist: The analyte binding the nanoparticles increases their size slowing their rotational Brownian motion. Alternatively, multiple nanoparticles can bind one or more epitopes on the analyte allowing the nanoparticles to aggregate again impacting their Brownian motion. Yet another alternative is for the regions on the analyte to bind both the nanoparticle and another larger nonmagnetic structure such as a bead or the nanocontainer. Yet another alternative is for the analyte to cleave or displace molecules binding the nanoparticles together or to another structure allowing the nanoparticles more freedom again impacting their Brownian motion. In all four cases the Brownian motion of the nanoparticle will be changed which will change the MSB signal allowing the changes to be measured remotely.

The ability of the nanoparticles to rotate freely can be measured in a sensitive way using Magnetic Spectroscopy of Brownian Motion (MSB). One implementation of an apparatus for MSB measurement is shown 150. This MSB apparatus has an amplifier 152 coupled to drive a drive coil 154 for providing an alternating magnetic field to nanoparticles 156 implanted or infused into subject 158. Pickup coil 160 and reverse-wound balancing coil 162 sense a response induced in the magnetic field by nanoparticles 156. The response is amplified by amplifier 164, digitized, and read by processor 166. The sensitivity of the system is achieved by measuring the harmonics of the drive frequency allowing very small signals to be measured because of the lack of other signals at the harmonic frequencies. In a typical embodiment, the frequency of alternating current applied to drive coil 154 is swept across many measured frequencies in a range of frequencies while responses are measured at each measured frequency to obtain a spectrum of the responses.

In an embodiment, the nanocontainers are self-assembled nanocontainers prepared according to Barjor Gimi, et al, *Cell encapsulation and oxygenation in nanoporous micro-containers* or for a similar product, *Biomed Microdevices*. 2009 December; 11(6): 1205-1212, (Gimi) available on the web at http://www.ncbi.nlm.nih.gov/pmc/articles/PMC2829986/pdf/nihms178484.pdf.

The nanocontainers of Gimi and utilized in this embodiment have two discrete components,
1) a hollow cubic base that is loaded with cells, and
2) a lid that closes the nanocontainer after it is filled with its magnetic nanoparticle payload.

The hollow cubic base comprises a 50 micron (μm) thick bottom face, and four 200 μm thick sidewalls on which a 50 μm 'female' structure is patterned to accommodate a corresponding 'male' structure formed in the lid. To create this cubic base, first a 50 μm thick SU-8 2025 (Microchem, Newton, Mass.) photoresist layer was spun on a Pyrex wafer. This SU-8 layer was patterned to form the bottom face of the hollowed cubic base. Next, 200 μm thick SU-8 2075 was spun, patterned and baked to form the four side walls of the hollowed cubic base. This 200 μm thick SU-8 layer was not photodeveloped to ensure uniform thickness of the next layer, a 50 μm thick SU-8 2025 which was patterned to form the female structure.

Figure 3:
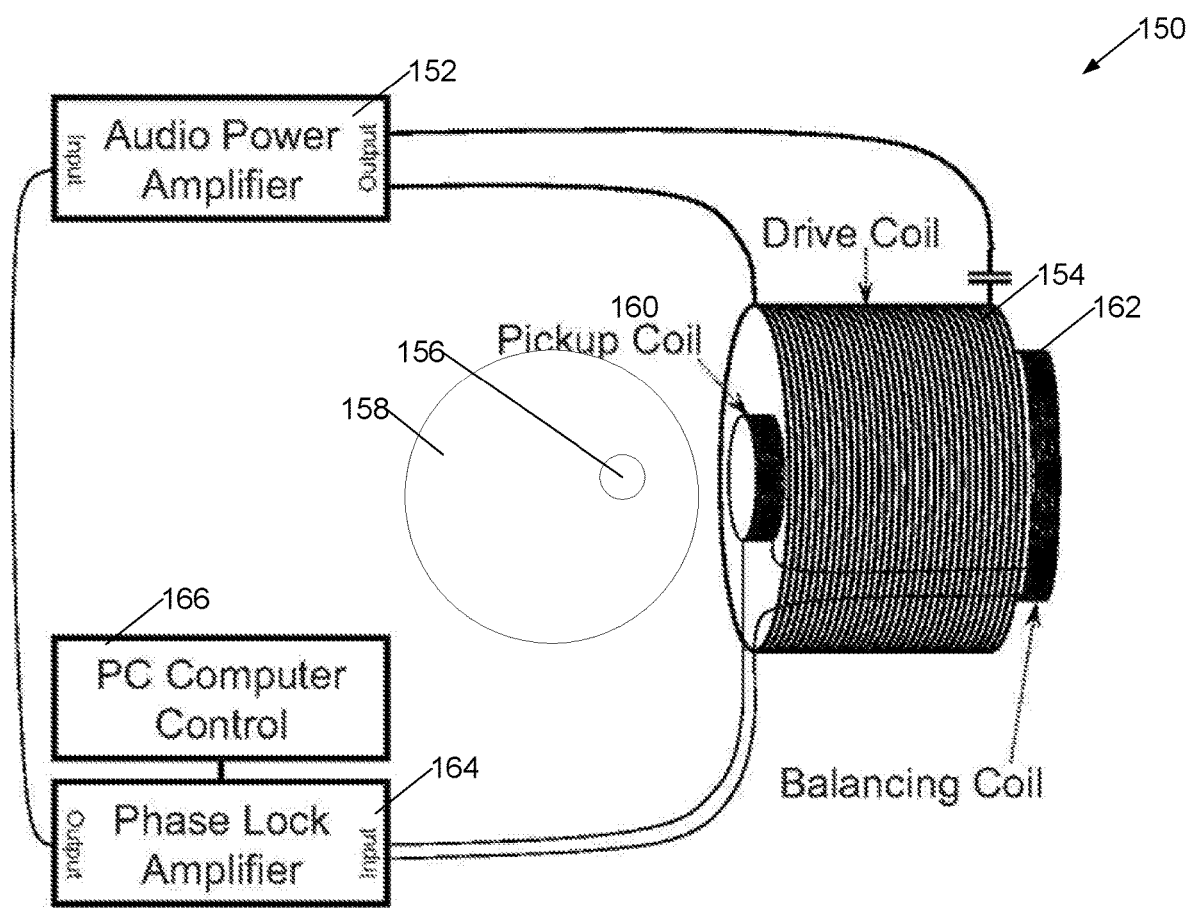
FIG. 3 is a block diagram of an apparatus for interrogating the nanoparticles within the nanocontainers to determine concentration of an analyte.

The SU-8 lid comprises a 100 μm thick rectangle for structural integrity, and a 35 μm male structure that interfaces with the female structure in the cubic base. Recessed within the lid is a matrix of cylindrical wells with a thin, semi-permeable nanoporous SU-8 membrane at the base of the wells. The thin membrane was devised to permit rapid and selective molecular transport. The lid fabrication was started with the deposition of a 4,000 Å Chromium (Cr) adhesion layer by electron beam evaporation. 2,000 Å thick Cr alignment marks were formed on top of the Cr coated wafer using a lift-off process. 350 nm thin SU-8 2000.5 was then spun and patterned to form the thin membrane for the formation of the nanopore arrays. Next, 70 nanometer (nm) Polymethyl methacrylate (PMMA) A2 photoresist was spun on the patterned 350 nm thin membrane and baked. The nanopore arrays were formed on the PMMA A2 layer by Electron Beam Lithography (EBL) using a 30 kV applied voltage, a 120 pA current and a 0.9 nC line dose. For each lid, 16 arrays of 1,680 nanopores, each of 1 μm length, were formed. To protect this patterned PMMA A2 during the etch process, 200 Å thick aluminum (Al) was deposited on the top and side walls using oblique-angle metal deposition. The 350 nm thin SU-8 membrane was etched by O2 plasma in reactive ion etch (RIE). The Al protection layer was then removed with Al etchant and the PMMA A2 layer was removed by acetone. This process resulted in the formation of very deep nanopores while retaining a small feature size and uniform cross section. Next, 100 μm thick SU-8 2075 was spun and patterned to form the main rectangular structure of the lid. 35 μm thick SU-8 2025 was then spun and patterned to form male structure on the periphery. Finally, the SU-8 lids were released from the wafer substrate using Cr wet etchant. The fabrication sequence for the microcontainer or nanocontainer lid is shown in FIG. 3. These nanocontainers and lids of Gimi are therefore formed of a polymer, in this embodiment of polymerized SU-8 photoresist.

Porous nanocontainers of other shapes may be fabricated, and porous nanocontainers may be fabricated from other materials, such as an alginate, as appropriate for each application.

In a particular embodiment, alginate nanocontainers are prepared using a commercial coaxial air flow bead generator procured from Nisco Engineering AG, Switzerland (www.nischo.ch). The unit comprises a nozzle, a coaxial air flow generator and a syringe pump for alginate infusion. The coaxial air stream pulls droplets of alginate-nanoparticle suspension from the nozzle and extrudes droplets of alginate mixed with nanoparticles into a gelling bath including $CaCl_2$, to form the containers. The nanocontainer is removed from the $CaCl_2$ solution when the nanocontainer wall is thick enough leaving the core gel. As the gel core inside the nanocontainer dissolves, the nanoparticles in the gel are left trapped in the core forming the nanoparticle filled nanocontainer. The nanocontainer size is controlled by varying the air flow and rate of injection of the alginate solution into the nozzle. A magnetic stirrer keeps the containers separated during gelling. Monodispersed alginate containers of the order of ~500 mm can be prepared by this method. Smaller containers can be prepared using an aerodynamic assisted bead generator, where the nozzle is enclosed under higher pressure using compressed air. As a result the diameter of the containers is compressed while exiting the orifice producing a smaller container size of about one tenth the size of the nozzle. Nanocontainers of the order of 10 nanometers can be prepared using a nozzle of about 100 nanometers in this way.

In another embodiment, a $CaCl_2$ (Calcium Chloride) solution with suspended nanoparticles in it is formed into droplets that are placed in an alginate solution to form the porous shell around the nanoparticles—the $CaCl_2$ hardening the alginate adjacent to the $CaCl_2$. Once the porous nanocontainer forms, remaining $CaCl_2$ diffuses out of the container leaving the nanoparticles inside.

For purposes of this document, nanoparticle means a magnetic particle having a largest dimension of between several nanometers and one millimeter ($1*10^{-8}$ to $1*10^{-3}$ meters) covalently or otherwise conjugated with a targeting molecule capable of binding an analyte or of being cleaved by an analyte. Generally the binding or cleaving is very specific for the targeted analyte.

For purposes of this document, nanocontainer means a container having a largest dimension of between several nanometers and one millimeter ($1*10^{-8}$ to $1*10^{-3}$ meters) and a volume of between $1*10^{-24}$ to $1.0*10^{-6}$ liters and capable of encapsulating one or more nanoparticles. A midrange nanocontainer means a nanocontainer having a largest dimension of between fifty microns and 0.15 millimeter ($5*10^{-5}$ to $1.5*10^{-34}$ meters) and a volume of between $1.25*10^{-10}$ to $3.375*10^{-9}$ liters. To avoid interference with MSB measurements of magnetic nanoparticles contained in the nanocontainers, it is preferable that the nanocontainers be formed from non-ferromagnetic materials such as, but not limited to, polymers and non-ferromagnetic metals.

In an embodiment, the nanoparticles are loaded into the nanocontainers by applying and closing the lids in a suspension of nanoparticles. Excess nanoparticles are then removed from the suspension by washing and filtering.

In an alternative embodiment, the porous nanocontainers are alginate beads containing the nanoparticles.

In other alternative embodiments, the nanocontainers or similar containers made of either the same or a different material that contains the nanoparticles and protects them from the immune system.

In an embodiment for in-vivo use, the nanocontainers are exposed to a fluid potentially containing the analyte by aspirating the nanocontainers into a syringe and injecting them subcutaneously into a living organism, such as a mammal or human subject, at an injection site; thereby exposing the nanocontainers to bodily fluids of the subject that potentially contain the analyte. In a particular embodiment, the nanocontainers are injected directly or indirectly into a lesion such as a tumor, where they may be used to monitor levels of analyte in the tumor environment. The apparatus for performing magnetic spectroscopy of Brownian motion (MSB) is then positioned adjacent to the injection site and a response is measured. Since the nanocontainers may remain embedded in the subject for some time, and ongoing monitoring of conditions within patient or tumor can be desirable, the apparatus for performing MSB may be removed, then re-positioned adjacent to the injection site or tumor at a later time and a further response is measured. In an alternative embodiment, a small, portable, MSB apparatus is left in place over tumor or injection site to make repeated measurements and send the information to a remote monitoring station. The MSB sensing apparatus detects agglutination or binding of the nanoparticles as a result of any analyte present in the fluid; a calibration table may be used to convert a measured MSB response to a determined analyte concentration. In an alternative embodiment, a set of calibration equations estimating the concentration in terms of MSB response is used to determine an analyte concentration from the MSB response.

In an alternative embodiment, for in-vivo use, the nanocontainers are delivered into the venous system or the capillaries or the small arteries of a living mammal, which may be a human, via injection into the blood stream from a catheter, syringe, or other mechanism. The nanocontainers are then transported by blood into small arterioles within a target organ or tumor of the mammal, where they lodge, and can thereupon be used to monitor levels of analyte within the target organ or tumor. In a particular embodiment, the nanocontainers are coated with anticoagulant to minimize fibrous clot formation.

In an alternative embodiment, for ex-vivo or in-vitro use, the nanocontainers or nanoparticles are deposited into a well of a multiple-well test plate; in a particular embodiment the nanocontainers are adhered to a floor of the well. A solution, which in an embodiment is plasma or blood, in another embodiment is an aqueous or alcoholic extract, and in another embodiment is a sample of a fluid such as drinking water, is added to the well such that the solution may penetrate the container and be exposed to the nanoparticles, after which MSB measurements are performed to measure an agglutination of the nanoparticles.

In an alternative embodiment, for ex-vivo or in-vitro use, the nanoparticles are deposited into a well of a multiple-well test plate. A solution, which in an embodiment is plasma or blood, in another embodiment is an aqueous or alcoholic extract, and in another embodiment is a sample of a fluid such as drinking water, is added to the well such that the solution is exposed to the nanoparticles, after which MSB measurements are performed to measure an agglutination of the nanoparticles. In another particular embodiment the nanoparticles are adhered to a floor of the well by the analyte after which the MSB measurements are performed to measure the rotational freedom of the nanoparticles. In another particular embodiment the nanoparticles are adhered to a floor of the well and cleaved from the well by the analyte after which the MSB measurements are performed to measure the rotational freedom of the nanoparticles.

In an embodiment, the nanoparticles are coated with a single type of selectively-binding molecule that selectively binds the analyte. In a particular embodiment the selectively-binding molecule is a protein, which in a particular embodiment is an antibody that selectively binds the analyte, or an enzyme, in another embodiment the selectively-binding molecule is an aptamer formed of deoxyribonucleic acid (DNA) or ribonucleic acid (RNA) having a particular nucleotide sequence.

In an alternative embodiment, a first portion of the nanoparticles are coated with a selectively-binding molecule that selectively binds a first region of the analyte and another portion of the nanoparticles are coated with a second selectively-binding molecule that selectively binds a second region of the analyte, thereby allowing a single molecule of analyte to bind two nanoparticles together. In a particular embodiment, the analyte is thrombin, and the selectively-binding molecules bind to separate sites on thrombin, and detection sensitivity of 3.5 picomolar has been obtained.

In an alternative embodiment, the nanoparticles are coated with a selectively-binding molecule that selectively binds a first region of the analyte and beads or nanocontainers are coated with a second selectively-binding molecule that selectively binds a second region of the analyte, thereby allowing a single molecule of analyte to bind a nanoparticle to a bead or nanocontainer.

In another particular embodiment, nanoparticles within the nanocontainers are linked to each other or to another bead or the nanocontainer itself with an indicator substance that can be attacked by an analyte. For example, but not limitation, in a particular embodiment the nanoparticles are bound with collagen 4. An enzyme MMP-9 is capable of cleaving the collagen-4 thereby separating the nanoparticles. The nanoparticles are exposed to a solution containing MMP-9, and a percentage of nanoparticles that become unbound is measured by using MSB techniques, thereby permitting quantification of MMP-9.

In a particular embodiment, the first portion and second portion of nanoparticles are of uniform size. In an alternative particular embodiment, the first portion of nanoparticles are particles of a first size and the second portion of nanoparticles are particles of a second size.

In an alternative embodiment, the nanocontainers are adhered onto a surface of a well of a test plate; a fluid potentially containing the analyte is then deposited into the well. The apparatus for performing MSB is then positioned adjacent to the well of the test plate, and a response is measured. The MSB sensing apparatus detects agglutination or binding of the nanoparticles as a result of any analyte present in the fluid as a difference in a measured MSB response from an MSB response of unbound, unagglutinated, nanoparticles; a calibration table may be used by a processor of the MSB sensing apparatus to convert a measured response to a determined analyte concentration.

In another alternative embodiment for ex-vivo or in-vitro use, the nanocontainers are adhered onto a surface of a test plate; a fluid potentially containing the analyte is then flowed over the plate. The apparatus for performing MSB is then positioned adjacent to the test plate, and an MSB response is measured; additional fluid may be continually flowed past the test plate and measurement of the MSB response is repeated periodically until an MSB response that meets alarm criteria is obtained, or until the test plate is determined to have expired. In this alternative embodiment, the apparatus may be used for screening large quantities of fluid, such as domestic tap water, in a fluid-handling apparatus for presence of a specific analyte, such as a toxin, chemical warfare agent, or other substance; when the analyte is, or becomes, present the MSB response meets the alarm criteria and an alarm condition may be reported and/or an operating mode of the fluid-handling apparatus may be changed. The MSB sensing apparatus detects agglutination or binding of the nanoparticles as a result of any analyte present in the fluid; a calibration table may be used to convert a measured response to a determined analyte concentration. In a particular embodiment, the nanoparticles are tagged with a synthetic DNA strand complimentary (or countersense) to an analyte DNA strand. Experiments show that concentrations of the analyte DNA strand of one nanomolar or less can be detected and quantified by exposing the nanoparticles to a solution containing the analyte DNA in vivo or in vitro. In a particular embodiment 12-pair nucleotide sequences are used that are complementary to a portion of an analyte DNA sequence.

In an embodiment using a streptavidin-biotin binding system, we found a detection limit of the MSB technique using our current apparatus is lower than 150 picomolar.

Figure 4:
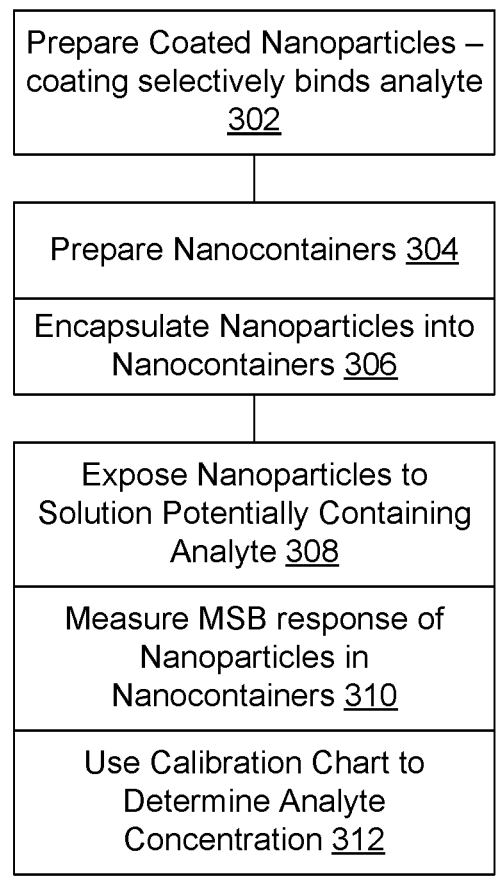
FIG. 4 is a flowchart of a method for measuring a concentration of an analyte using coated nanoparticles bound in nanocontainers.

A method for using nanocontainer-bound nanoparticles for sensing an analyte is illustrated in FIG. 4. Magnetic nanoparticles are coated 302 with a substance, such as a protein or a nucleic acid chain, that selectively binds an analyte as previously discussed. Nanocontainers are then prepared 304. The nanoparticles are then encapsulated 306 into the nanocontainers. The nanocontainers are then exposed 308 to a solution that potentially may contain the analyte, which in some embodiments is done by injecting nanocontainers into a living mammal or human subject, and in other embodiments is done by binding nanocontainers on a plate and adding solution. The MSB response of the nanoparticles is then measured 310. Measured MSB response is used 312 to find an analyte concentration by using a calibration chart.

While most of the foregoing discussion references nanoparticles in the nanocontainers becoming bound when exposed to analyte, or released by an enzymatic reaction, in another embodiment, nanoparticles tagged with a selective binding aptamer or protein (including antibodies) are bound by exposure to an indicator substance that includes a linking molecule having multiple binding sites resembling a binding site of an analyte. The nanocontainers and nanoparticles may then be desiccated and stored, then rehydrated, and may be injected into a subject, placed in a test-plate well, or bound to a test plate. The nanoparticles are then exposed to a solution that may contain analyte. In this embodiment exposure of nanoparticles to the analyte displaces the linking indicator-substance molecules through competitive binding or higher affinity bonding of analyte to the selective binding aptamer or protein, thereby releasing agglutinated nanoparticles from each other, or from nanocontainer walls. Releasing agglutinated nanoparticles from their pre-analyte agglutinated or aggregated state causes a detectable change in MSB response that can be quantified and used to determine analyte exposure or analyte concentration.

Figure 5:
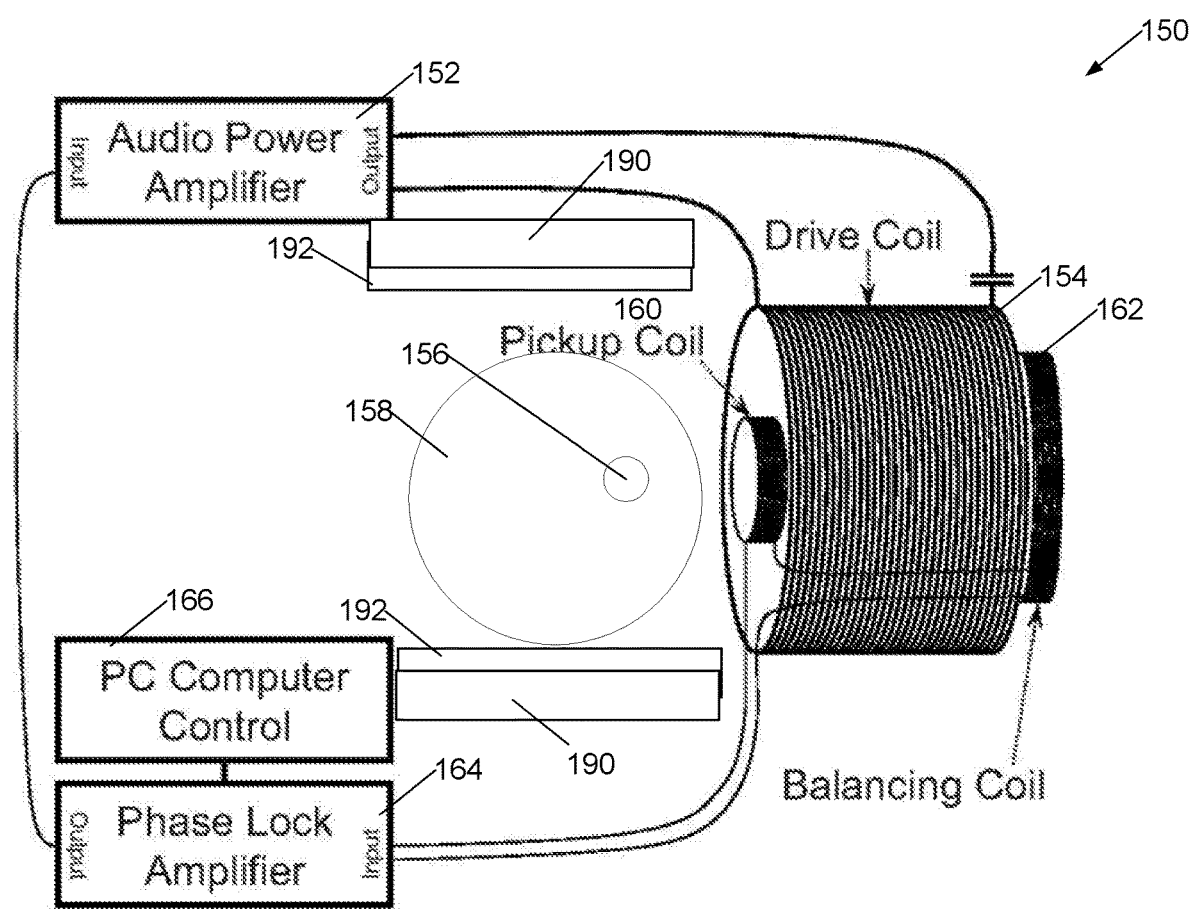

In another embodiment, with reference to FIG. 5, bias-field 190 and complementary sweep 192 magnets are added to the MSB detection apparatus. If the bias-field magnet is strong enough to saturate the magnetic nanoparticles—drowning out MSB measurement, but adjustable sweep magnets are strong enough to create a zone of near-zero bias field where an MSB response can be measured, the zone of near-zero field can be positioned at will within a subject. MSB signal from encapsulated nanoparticles in the near-zero field position can be determined, while MSB signals from elsewhere in the subject can be excluded from the measurement. By changing field in sweep magnets, the zone of near-zero field can be moved through the subject, allowing MSB signals to be determined, and both magnetic nanoparticle concentration and analyte concentration determined, at multiple positions within the subject. These multiple concentrations are then mapped and displayed as a tomographic image.

Combinations

The herein-described nanoporous nanocontainers containing magnetic particles, and their use to measure an analyte, may be used in a variety of ways with a variety of analytes. In particular, some of the combinations are as follows.

A system designated A for measuring an analyte concentration in a solution has multiple nanocontainers each having porous walls, at least some nanocontainers containing a plurality of magnetic nanoparticles, the magnetic nanoparticles coated with a selective binder capable of selectively binding a substance selected from the group consisting of the analyte, and an indicator substance releasable from the selective binder by the analyte, and an indicator substance cleavable by the analyte, apparatus for exposing the nanocontainers to the solution, and magnetic spectroscopy of Brownian motion sensing apparatus for detecting agglutination or aggregation of the nanoparticles.

A system designated AA including the system designated A wherein the selective binder is selected from the group consisting of a nucleic acid strand, a protein, and a combination of nucleic acid strands and protein.

A system designated AB including the system designated A or AA wherein the nanocontainers are of less than one millimeter in largest dimension.

A system designated AC including the system designated AB, A or AA wherein the nanocontainers are midsize nanocontainers having average size less than 150 microns in largest dimension.

A system designated AD including the system designated A, AA, AB, or AC wherein the nanocontainers are formed of photoresist.

A system designated AE including the system designated A, AA, AB, or AC where the nanocontainers are formed of an alginate.

A system designated AF including the system designated A, AA, AB, AC. AD, or AE where the apparatus for exposing the nanocontainers to the solution comprises apparatus for injecting the nanocontainers into a living mammal.

A system designated AG including the system designated A, AA, AB, AC, AD, AE, or AF where the apparatus for exposing the nanocontainers to the solution comprises a test plate to which nanocontainers are adhered.

A system designated AGA including the system designated A, AA, AB, AC, aD, AE, or AF, where the apparatus for exposing the nanoparticles to the solution comprises a well of a multiple-test plate within which nanocontainers with nanoparticles are deposited.

A system designated AH including the system designated A, AA, AB, AC, AD, AE, AF, AG, or AGA where the selective binder is a nucleic-acid chain.

A system designated AI including the system designated A, AA, AB, AC, AD, AE, AF, AG, or AGA where the selective binder is a protein.

A system designated AJ including the system designated A, AA, AB, AC, AD, AE, AF, AG, or AGA where the selective binder is an antibody.

A system designated AK including the system designated A, AA, AB, AC, AD, AE, AF, AG, AGA, or AK, wherein the selective binder is configured to bind analyte.

A system designated AL including the system designated A, AA, AB, AC, AD, AE, AF, AG, AGA, or AK, further comprising an indicator substance and wherein the selective binder is configured to bind the indicator substance in such a way that the analyte can displace indicator substance from the selective binder.

A system designated AM including the system designated A, AA, AB, AC, AD, AE, AF, AG, AGA, or AK, further comprising an indicator substance and wherein the indicator substance is cleavable by the analyte.

A method designated B of determining a concentration of an analyte in a fluid including coating a plurality of magnetic nanoparticles with a selective binder selected from the group consisting of a protein and or a nucleic acid and capable of binding a substance selected from the group consisting of the analyte, and an indicator substance releasable from the selective binder by the analyte, and an indicator substance cleavable by the analyte; encapsulating the magnetic nanoparticles in porous nanocontainers; exposing the nanocontainers to the fluid; using magnetic spectroscopy of Brownian motion sensing apparatus to determine an MSB response dependent upon agglutination or binding of the nanoparticles.

A method designated BA including the method designated B wherein the step of using magnetic spectroscopy of Brownian motion sensing apparatus to determine an MSB response is repeated over a period of time.

A method designated BB including the method designated BA further including determining an alarm condition based upon the MSB response.

A method designated BC including the method designated B, BA, or BB further comprising injecting the porous nanocontainers into a living mammal, and wherein the fluid is a bodily fluid of the living organism.

A method designated BD including the method designated B, BA, BB or BC wherein the nanocontainers are of less than one millimeter in largest dimension.

A method designated BE including the method designated BD wherein the nanocontainers are midsize nanocontainers having average size less than 150 microns in largest dimension.

A method designated BF including the method designated B, BA, BB, BC, BD, or BE where the nanocontainers are formed of polymer.

A method designated BG including the method designated B, BA, BB, BC, BD, or BE where the nanocontainers are formed of an alginate.

A system designated C for measuring an analyte concentration a plurality of magnetic nanoparticles, the magnetic nanoparticles coated with a selective binder capable of selectively binding a substance selected from the group consisting of the analyte, an indicator substance releasable from the selective binder by the analyte, and an indicator substance cleavable by the analyte, apparatus for exposing the nanocontainers to the solution, and magnetic spectroscopy of Brownian motion sensing apparatus for detecting agglutination or aggregation of the nanoparticles.

A system designated CA including the system designated C, wherein the selective binder binds an indicator substance.

A system designated CB including the system designated CA or C, where the apparatus for exposing the nanoparticles to the solution comprises a well of a multiple-test plate within which nanocontainers with nanoparticles are deposited.

A system designated CC including the system designated CA, C, or CB where the selective binder is a nucleic-acid chain.

A system designated CD including the system designated C, CA, or CB where the selective binder is a protein.

A system designated CE including the system designated CD where the selective binder is an antibody.

A system designated CF including the system designated C, CA, CB, CC, CD or CE, wherein the selective binder is configured to bind analyte and wherein the selective binder is configured to bind the indicator substance in such a way that the analyte can displace indicator substance from the selective binder.

A system designated CG including the system designated C, CA, CB, CC, CD, or CE, wherein the indicator substance is cleavable by the analyte.

While the invention has been particularly shown and described with reference to a preferred embodiment thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. A system for measuring an analyte concentration in a solution comprising:
    a plurality of nanocontainers having porous walls, the nanocontainers containing a plurality of magnetic nanoparticles, the magnetic nanoparticles coated with a selective binder capable of selectively binding a substance selected from the group consisting of the analyte, an indicator substance releasable from the selective binder by the analyte, and an indicator substance cleavable by the analyte;
    apparatus for exposing the nanocontainers to the solution; and
    magnetic spectroscopy of Brownian motion (MSB) sensing apparatus for detecting agglutination or aggregation of the nanoparticles;
    wherein the selective binder capable of selectively binding a substance is selected from the group consisting of a nucleic acid strand, a protein, and a combination of nucleic acid strands and protein;
    wherein the nanocontainers are nanocontainers having average size less than 150 microns in largest dimension;
    the MSB sensing apparatus comprising:
    apparatus configured to drive a drive coil adapted to provide an alternating magnetic field at a drive frequency to the magnetic nanoparticles, a pickup coil and a reverse-wound balancing coil configured to sense a response induced in the magnetic field by the magnetic nanoparticles,
    the pickup coil and balancing coil coupled through an amplifier to a processor, the processor configured to measure harmonics of the drive frequency.

2. The system of claim 1 wherein the drive frequency is swept across a plurality of measured frequencies in a range of frequencies while responses are measured at each measured frequency to obtain a spectrum of responses induced in the magnetic field by the magnetic nanoparticles.

3. The system of claim 2, further comprising bias field magnets configured to apply a bias field to a living mammal, and wherein the bias field is swept to map both magnetic nanoparticle concentration and analyte concentration at multiple positions within the living mammal, where the apparatus for exposing the nanocontainers to the solution comprises apparatus for injecting the nanocontainers into the living mammal.

4. The system of claim 2, where the apparatus for exposing the nanocontainers to the solution comprises a test plate to which nanocontainers are adhered.

5. The system of claim 4 where the selective binder capable of selectively binding a substance is a nucleic-acid chain.

6. The system of claim 4, where the selective binder capable of selectively binding a substance is a protein.

7. The system of claim 6 where the selective binder capable of selectively binding a substance is an antibody.

8. The system of claim 3 where the selective binder capable of selectively binding a substance is a nucleic-acid chain.

9. The system of claim 7, where the selective binder capable of selectively binding a substance is a protein.

10. The system of claim 6 where the selective binder capable of selectively binding a substance is an antibody.

11. The system of claim 2, where the apparatus for exposing the nanocontainers to the solution comprises apparatus for injecting the nanocontainers into a living mammal.

12. The system of claim 1, where the apparatus for exposing the nanocontainers to the solution comprises a test plate to which nanocontainers are adhered.

13. The system of claim 12 where the selective binder capable of selectively binding a substance is a nucleic-acid chain.

14. The system of claim 12, where the selective binder capable of selectively binding a substance is a protein.

15. The system of claim 14 where the selective binder capable of selectively binding a substance is an antibody.

16. The system of claim 1 where the selective binder capable of selectively binding a substance is a nucleic-acid chain.

17. The system of claim 1, where the selective binder capable of selectively binding a substance is a protein.

18. The system of claim 17 where the selective binder capable of selectively binding the analyte is an antibody.

19. The system of claim 1 wherein the nanocontainers are fabricated from photoresist.

20. The system of claim 19 wherein the photoresist comprises polymethyl methacrylate.

21. The system of claim 2 further comprising bias field magnets configured to apply a bias field to a living mammal, and wherein the bias field is swept to map both magnetic nanoparticle concentration and analyte concentration at multiple positions within the living mammal.

* * * * *